(12) United States Patent
Shahar et al.

(10) Patent No.: US 11,291,785 B2
(45) Date of Patent: Apr. 5, 2022

(54) PORTABLE LIGHT-WEIGHT VENTILATOR SYSTEM

(71) Applicant: INOVYTEC MEDICAL SOLUTIONS LTD, Hod Hasharon (IL)

(72) Inventors: Mark Shahar, Holon (IL); Nir Barkai, Kfar Saba (IL)

(73) Assignee: INOVYTEC MEDICAL SOLUTIONS LTD, Hod Hasharon (IL)

( * ) Notice: Subject to any disclaimer, the term of this patent is extended or adjusted under 35 U.S.C. 154(b) by 277 days.

(21) Appl. No.: 16/078,345

(22) PCT Filed: Feb. 27, 2017

(86) PCT No.: PCT/IL2017/050249
§ 371 (c)(1),
(2) Date: Aug. 21, 2018

(87) PCT Pub. No.: WO2017/149532
PCT Pub. Date: Sep. 8, 2017

(65) Prior Publication Data
US 2019/0054265 A1 Feb. 21, 2019

Related U.S. Application Data

(60) Provisional application No. 62/300,933, filed on Feb. 29, 2016.

(51) Int. Cl.
*A61M 16/00* (2006.01)
*A61M 16/08* (2006.01)
(Continued)

(52) U.S. Cl.
CPC ...... *A61M 16/0066* (2013.01); *A61M 16/024* (2017.08); *A61M 16/0816* (2013.01);
(Continued)

(58) Field of Classification Search
CPC .......... A61M 16/0066; A61M 16/0883; A61M 16/101; A61M 16/205; A61M 16/0816;
(Continued)

(56) References Cited

U.S. PATENT DOCUMENTS 3,933,171 A 1/1976 Hay
4,206,754 A * 6/1980 Cox ..................... A61M 16/024
128/204.21
(Continued)

FOREIGN PATENT DOCUMENTS

CN 101745171 A 6/2010
CN 102580201 A 7/2012
(Continued)

OTHER PUBLICATIONS

Written opinion of the international searching authority for PCT/IL2017/050249, dated May 29, 2017 (5 pages).
(Continued)

*Primary Examiner* — Rachel T Sippel
*Assistant Examiner* — Kelsey E Baller
(74) *Attorney, Agent, or Firm* — Roach, Brown, McCarthy & Gruber, P.C.; Kevin D. McCarthy

(57) ABSTRACT

A ventilator system for providing respiratory support in cases of acute respiratory failure or severe trauma is described. The ventilator system has a ventilator and a tubing system. The system is characterized in that the ventilator has a continuous bleed valve configured to be open to air flow from the blower at all times when the blower is operating during both inspiration and expiration; thereby providing a minimal amount of pressure within a patient's lungs at the end of each exhalation—positive end expiratory pressure (PEEP). In an embodiment of the invention the system comprises a manifold block configured to hold the main operating elements of the ventilator.

20 Claims, 13 Drawing Sheets

(51) Int. Cl.
*A61M 16/20* (2006.01)
*A61M 16/10* (2006.01)

(52) U.S. Cl.
CPC ...... *A61M 16/0883* (2014.02); *A61M 16/101* (2014.02); *A61M 16/204* (2014.02); *A61M 16/205* (2014.02); *A61M 16/206* (2014.02); *A61M 16/006* (2014.02); *A61M 16/209* (2014.02); *A61M 2016/0021* (2013.01); *A61M 2016/0027* (2013.01); *A61M 2016/0036* (2013.01); *A61M 2205/3306* (2013.01); *A61M 2205/3375* (2013.01); *A61M 2205/50* (2013.01); *A61M 2230/60* (2013.01)

(58) Field of Classification Search
CPC .............. A61M 16/204; A61M 16/206; A61M 16/024; A61M 16/006; A61M 16/209; A61M 16/00; A61M 16/0057–0084; A61M 2205/3375; A61M 2205/3306; A61M 2205/50; A61M 2230/60; A61M 2016/0027; A61M 2016/0036; A61M 39/00; A61M 39/22–288; A61M 2202/02; A61M 2202/0208; A61M 2202/0241
USPC .................................................. 128/204.21
See application file for complete search history.

(56) References Cited

U.S. PATENT DOCUMENTS

| | | | |
|---|---|---|---|
| 4,651,731 A | 3/1987 | Vicenzi | |
| 5,682,877 A * | 11/1997 | Mondry | A61M 16/0627 128/204.23 |
| 5,706,830 A * | 1/1998 | Parker | A61M 16/0054 128/203.12 |
| 5,954,051 A * | 9/1999 | Heinonen | A61M 16/024 128/205.24 |
| 6,009,871 A * | 1/2000 | Kiske | A61M 16/024 128/203.12 |
| 6,588,421 B1 * | 7/2003 | Diehl | A61M 16/12 128/201.13 |
| 6,802,225 B2 | 10/2004 | Shahar | |
| 8,118,024 B2 | 2/2012 | DeVries | |
| 9,180,266 B1 * | 11/2015 | Sherman | A61M 16/0003 |
| 2002/0014239 A1 * | 2/2002 | Chalvignac | A61M 16/205 128/204.18 |
| 2002/0053345 A1 * | 5/2002 | Jafari | A61M 16/0069 128/204.23 |
| 2003/0172931 A1 * | 9/2003 | Kerechanin, II | A61M 16/00 128/204.18 |
| 2008/0223368 A1 * | 9/2008 | Hoffmann | A61M 16/20 128/205.24 |
| 2009/0145428 A1 | 6/2009 | Sward et al. | |
| 2009/0260628 A1 * | 10/2009 | Flynn, Sr. | A61M 16/0078 128/203.28 |
| 2011/0232640 A1 | 9/2011 | Van Dijk | |
| 2012/0060837 A1 * | 3/2012 | Liu | A61M 16/204 128/204.21 |
| 2012/0174925 A1 | 7/2012 | Tham | |
| 2014/0150796 A1 * | 6/2014 | Milne | A61M 16/024 128/205.23 |
| 2015/0290418 A1 * | 10/2015 | Kaczka | A61M 16/18 128/200.14 |

FOREIGN PATENT DOCUMENTS

| | | |
|---|---|---|
| CN | 102802709 A | 11/2012 |
| CN | 105013057 A | 11/2015 |
| JP | 2011-505906 A | 3/2011 |
| WO | 2000/045883 A1 | 8/2000 |
| WO | 2010/148412 A1 | 12/2010 |
| WO | 2011041838 A1 | 4/2011 |

OTHER PUBLICATIONS

International search report for PCT/IL2017/050249, dated May 29, 2017 (3 pages).
Communication and Supplementary European Search Report for EP 17 75 9377, dated Sep. 24, 2019; 8 pages.
Office action from the Chinese Patent Office in a counterpart foreign application (201780013722.2) dated Jul. 3, 2020 (9 pages), English language machine translation thereof (7 pages), and English language translated search report (1 page).
Office action from the Indian Patent Office for application No. 201827033958; dated Aug. 23, 2021; 6 pages.

* cited by examiner

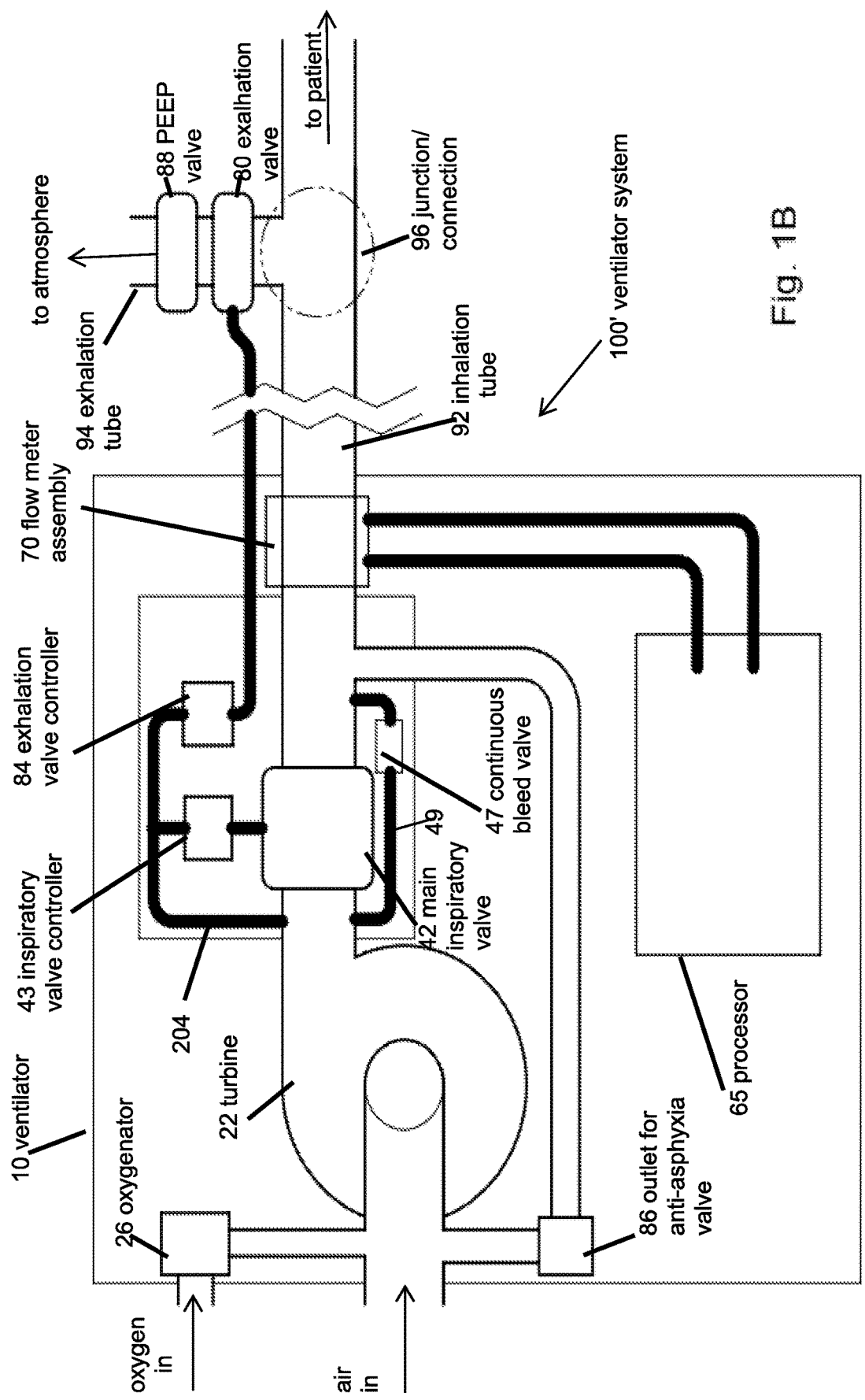

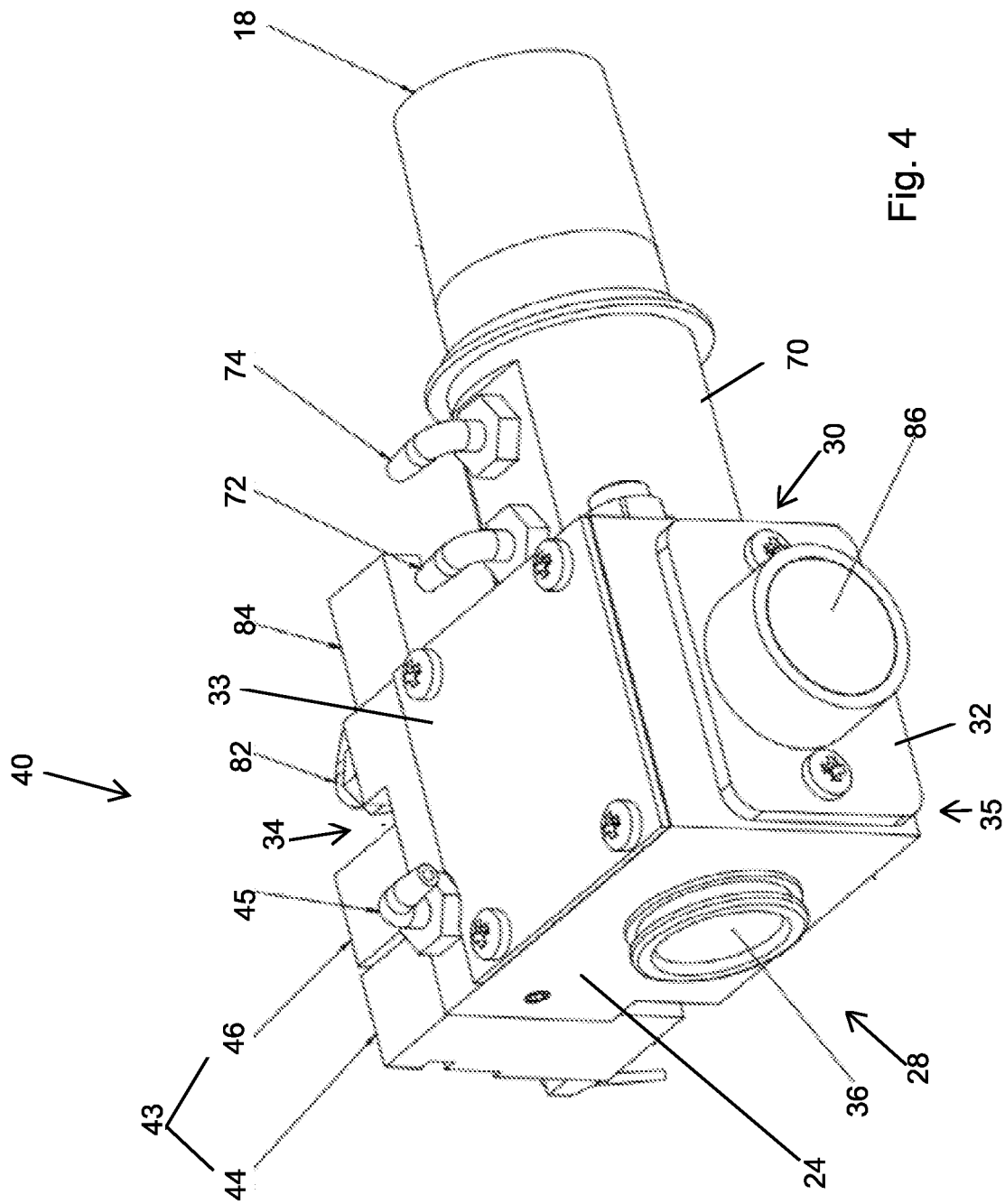

PORTABLE LIGHT-WEIGHT VENTILATOR SYSTEM

FIELD OF THE INVENTION

The invention is from the field of medical devices. Specifically the invention is directed to a ventilator system for providing respiratory support in cases of acute respiratory failure or severe trauma.

BACKGROUND OF THE INVENTION

Positive pressure ventilators work by forcing air through a drive mechanism, which raises the pressure in the patient's airways relative to atmospheric pressure, which consequently causes the lungs to expand. Currently known ventilators which are suitable for providing such respiratory support are generally large and heavy (on an order of about 3.5-10 kilograms), and may require a separate oxygen cylinder for the pneumatic operation of the device, which adds to the overall transport weight. Moreover, there are many technical problems which must be overcome and for which suitable solutions have not yet been found. For example, it is necessary to provide for a minimal amount of pressure within the patient's lungs at the end of each exhalation, known as positive end expiratory pressure (PEEP). Known ventilators control PEEP in various ways, such as controlling an external pilot operated valve or valves installed inside the ventilator allowing the gases in the patient's lungs to be released, or by controlling the expiratory pressure by proportionally controlling a pilot operated valve attached to the patient circuit expiratory limb (or to a one limb circuit). In addition, in known turbine operated ventilators it is difficult to support quick spontaneously initiated breaths to the patient (also called triggered breaths or spontaneous breaths), which could be important, for example, in instances wherein a rapid breath is required.

U.S. Patent Publication Number 2011/0232640 to Van Dijk et al. teaches a blower driven ventilator having a valve assembly, and a system and method for controlling the valve assembly during ventilation. However, the valve assembly disclosed therein provides for a particular PEEP control mechanism which relies on "returning" air to the patient, which may not be an optimal method for controlling PEEP due to central processor unit (CPU) resources, the need to compensate for very small leaks with either acceleration of the turbine hence wasting energy resources, or having to open a very small gap between the housing and orifice through which flow from the turbine is forced in the direction of the patient. Additionally, the valve assembly disclosed therein requires a connection to ambient air in the valve assembly itself, which may result in the need for accelerating the blower rotor for compensation of leak, and/or accumulation of CO2.

U.S. Pat. No. 8,118,024 to DeVries et al. discloses a portable ventilator having a bias valve to facilitate closing of an exhalation valve at the start of inspiration and to regulate PEEP. The bias valve in this case is used in order to attenuate pulsating gas flow produced by a ROOTS® blower. The dynamic response of this valve operates based on a preloaded force causing a hysteresis curve, i.e. when the bias pressure is set to 4 cmH$_2$O, the flow rate is allowed to go to 4 liters per minute (1 pm). This system may have several disadvantages, including fluctuations in flow and/or pressure, a required fast response control system (order of magnitude of 10 msec response time), and relatively high electrical consumption due to a directly operated actuator.

It is therefore a purpose of the present invention to provide a lightweight, portable, ventilator that can optimally control PEEP and inspiratory rates with minimal energy consumption.

Further purposes and advantages of this invention will appear as the description proceeds.

SUMMARY OF THE INVENTION

In a first aspect the invention is a positive pressure ventilator system for providing respiratory support to a patient. The ventilator system is comprised of: (a) a ventilator comprising a source of pressurized air, a manifold block, and a continuous bleed aperture; and (b) a tubing system connected to the ventilator and to the patient. The ventilator system is characterized in that, at all times while the source of pressurized air is operating to provide pressurized air to the ventilator, the ventilator provides a continuous flow of air via the continuous bleed aperture to the tubing system.

In embodiments of the ventilator system the source of pressurized air comprises one of the following: a pressurized gas generator, a pressurized gas cylinder, a piston pump, a multi vein pump, a roots blower, a gear pump, a voice coil assembly, a centrifugal pump, a diaphragm pump, a radial blower, a single stage turbine, and a multi stage turbine.

In embodiments of the ventilator system the manifold block holds the main operating components of the ventilator. The manifold block comprises within its interior a main inspiratory valve, the continuous bleed aperture, and at least most of the tubes and wires needed for fluidly connecting and operating the main operating components of the ventilator and, attached to its exterior surfaces an inspiratory valve controller and an exhalation valve controller.

In embodiments of the ventilator system the inspiratory valve controller and the exhalation valve controller each comprise at least one solenoid valve.

Embodiments of the ventilator system comprise a flow meter assembly, which is located at one of the following locations in the system: within the ventilator housing between the source of pressurized air and the manifold block; within the ventilator housing between the manifold block and the tubing system; and on the tubing system. The flow meter assembly can be one of: a Venturi flow meter; a hot wire anemometer; an impeller flow meter; an ultrasonic flow meter; and an optical flow meter.

In embodiments of the ventilator system the tubing system includes an inhalation tube and an exhalation tube, which in a one limb ventilator are the same tube; and, in the case of two limb ventilator, a junction/connector connecting inhalation tube to exhalation tube and leading to the patient. In embodiments of the ventilator system the exhalation tube comprises an exhalation valve.

Embodiments of the ventilator system comprise a PEEP valve located at one of the following places in the system: downstream from the exhalation valve, upstream from the exhalation valve; and in a combined assembly with the exhalation valve.

In embodiments of the ventilator system the ventilator comprises at least one of: an oxygenator; an anti-asphyxia valve; a safety valve; a bypass solenoid that rapidly decreases the pressure to the patient; a solenoid disconnecting the PEEP valve in case there is continuous high pressure in the source of pressurized air; and a solenoid connected to a nebulizer system.

In embodiments of the ventilator system the ventilator comprises a processor. In these embodiments the processor is configured to provide for operation of the inspiratory valve controller, the exhalation valve controller and combinations thereof based on input from a user and/or an algorithm or multiple algorithms and is also configured to set levels of oxygen enrichment, tidal volume, number of breaths per minute, maximum peak inspiratory pressure (PIP), and positive end expiratory pressure (PEEP), wherein at least one of these parameters may be fixed or adjustable.

In embodiments of the ventilator system the continuous bleed aperture comprises one or both of a small diameter hole and a proportional solenoid bleed valve.

In embodiments of the ventilator system the volume of air flow through the continuous bleed aperture ranges from 1% to 10% of the volume of air flow through the main inspiratory valve.

In embodiments of the ventilator system the ratio of the free flow area of the continuous bleed aperture to the free flow area of the main inspiratory valve is 2 mm$^2$ to 400 mm$^2$.

In embodiments of the ventilator system the continuous bleed aperture has a diameter of between 0.5 and 2.5 mm, which results in a volumetric flow rate of between 2 and 20 liters per minute under free flow conditions, based on pressures of between 5 and 50 cmH$_2$O.

In embodiments of the ventilator system during an inspiratory cycle the exhalation valve is closed to air flow and a stream of air flowing through the main inspiratory valve combines with a stream of air flowing through the continuous bleed aperture and the combined streams flow through the inhalation tube past the junction/connector to the patient.

In embodiments of the ventilator system during an expiratory cycle the main inspiratory valve is closed to air flow and a stream of air flowing through the continuous bleed aperture flows into the inhalation tube past the junction/connector and combines with a stream of exhaled air flowing from the patient into exhalation tube and the combined streams flow through the exhalation valve and the PEEP valve out into ambient air.

In embodiments of the ventilator system the manifold block is located inside the source of pressurized air.

In embodiments of the ventilator system the manifold block has a volume in the range of 15 to 100 cm$^3$.

In embodiments of the ventilator system the weight of the ventilator is in a range of 0.6-1.6 Kg.

In embodiments of the ventilator system the main inspiratory valve works by activating a diaphragm to move up and down to cause opening and closing of a fluid passage.

In a second aspect the invention is a manifold block for use in a positive pressure ventilator system for providing respiratory support to a patient. The manifold block comprises, within its interior, a main inspiratory valve, a continuous bleed aperture, and at least most of the tubes and wires needed for connecting and operating the main operating components of the ventilator.

Embodiments of the manifold block comprise an inspiratory valve controller and an exhalation valve controller attached to its exterior surfaces.

In embodiments of the manifold block the continuous bleed aperture comprises one or both of a small diameter hole and a proportional solenoid bleed valve.

In embodiments of the manifold block the volume of air flow through the continuous bleed aperture ranges from 1% to 10% of the volume of air flow through the main inspiratory valve.

In embodiments of the manifold block the ratio of the free flow area of the continuous bleed aperture to the free flow area of the main inspiratory valve is 2 mm$^2$ to 400 mm$^2$.

Embodiments of the manifold block have a volume in the range of 15 to 100 cm$^3$.

In a third aspect the invention is a method of maintaining a predetermined value of positive end expiratory pressure (PEEP) within the respiratory passageway of a patient connected to a positive pressure ventilator system. The ventilator system is comprised of: a source of pressurized air; a main inspiratory valve; an inhalation tube; an exhalation tube; an exhalation valve; a PEEP valve; a processor; and a continuous bleed aperture. The method comprising activating the source of pressurized air and configuring the processor to control the valves in the ventilator system such that:

a) during an inspiratory cycle—the main inspiratory valve is opened to air flow, the exhalation valve is closed to air flow, and the continuous bleed aperture is opened to air flow, whereupon a stream of air flowing through the main inspiratory valve combines with a stream of air flowing through the continuous bleed aperture and the combined streams flow through the inhalation tube to the patient; and b) during an expiratory cycle—the main inspiratory valve is closed to air flow, the exhalation valve is opened to air flow, and the continuous bleed aperture is opened to air flow, whereupon a stream of air flowing through the continuous bleed aperture flows into the inhalation tube and combines with a stream of exhaled air flowing from the patient into the exhalation tube and the combined streams flow through the exhalation valve and, whenever the pressure is above the predetermined value of PEEP, the combined streams flow through the PEEP valve out into ambient air.

In embodiments of the method the continuous bleed aperture comprises one or both of a small diameter hole and a proportional solenoid bleed valve.

In embodiments of the method the volume of air flow through the continuous bleed aperture ranges from 1% to 10% of the volume of air flow through the main inspiratory valve.

In embodiments of the method the ratio of the free flow area of the continuous bleed aperture to the free flow area of the main inspiratory valve is 2 mm$^2$ to 400 mm$^2$.

In embodiments of the method the ratio of the free flow area of the continuous bleed aperture to the free flow area of the main inspiratory valve is 2 mm$^2$ to 400 mm$^2$.

All the above and other characteristics and advantages of the invention will be further understood through the following illustrative and non-limitative description of embodiments thereof, with reference to the appended drawings.

BRIEF DESCRIPTION OF THE DRAWINGS

FIG. 2A and FIG. 2B schematically show block diagram illustrations of FIG. 1A and FIG. 1B respectively, further depicting the flow of air during an inspiratory cycle;

FIGS. 4 and 5 schematically show perspective illustrations of a manifold block assembly with an attached flow meter assembly in the ventilator of FIG. 1B shown from different viewing angles;

DETAILED DESCRIPTION OF EMBODIMENTS OF THE INVENTION

Figure 1A:
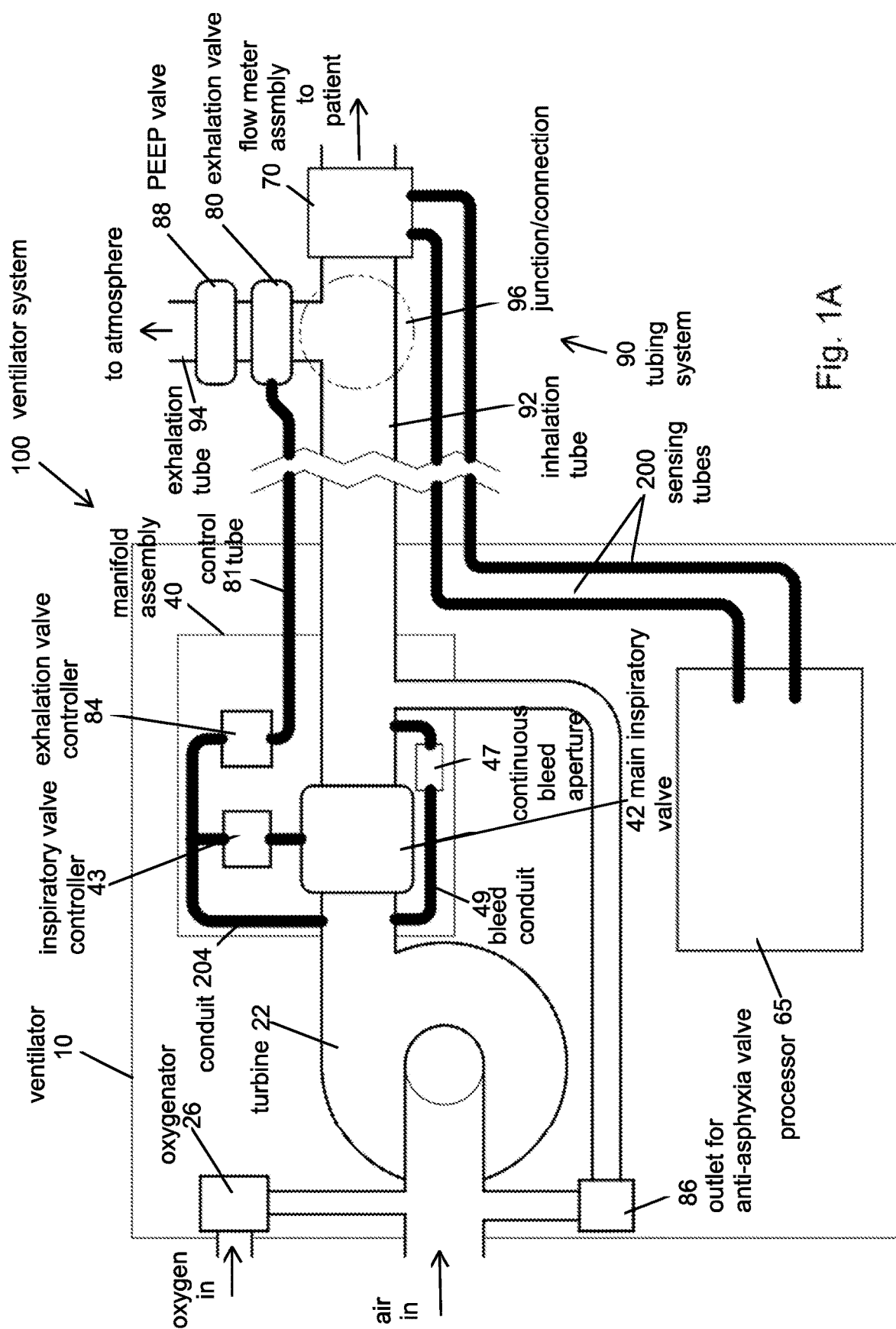
FIG. 1A and FIG. 2A schematically show block diagram illustrations of embodiments of a ventilator system.

In the following detailed description, numerous specific details are set forth in order to provide a thorough understanding of the present invention. It will be understood by those of ordinary skill in the art that embodiments of the present invention may be practiced without these specific details. In other instances, well-known methods, procedures, components and structures may not have been described in detail so as not to obscure the present invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Reference is now made to FIG. 1A, which is a block diagram illustration of an embodiment of a ventilator system, in accordance with embodiments of the present invention. Ventilator system 100 includes a ventilator 10 and a tubing system 90 for connecting ventilator 10 to a patient. Ventilator 10 includes a source for providing pressurized gas, e.g., air to the patient called herein turbine 22 for simplicity although a person skilled in the art will appreciate that the pressurized gas may alternatively be provided by any pressurized gas generator/supply. Examples of suitable "turbines" include, but are not limited to, a pressurized gas cylinder, a piston pump, multi vein pump, roots blower, gear pump, voice coil assembly, centrifugal pump, diaphragm pump, radial blower, a single stage turbine, multi stage turbine or any other blower commonly known in the art. Turbine 22 is connected to manifold assembly 40. Manifold assembly 40 comprises a main inspiratory valve 42 and a continuous bleed aperture 47. Main inspiratory valve 42 is controlled by an inspiratory valve controller 43, e.g. a solenoid valve. In some embodiments, inspiratory valve controller 43 includes one or more inspiratory valve controllers.

In the embodiment shown in FIG. 1 a manifold assembly 40 is connected to a flow meter assembly 70, which is positioned outside of ventilator 10 on tubing assembly 90. The flow meter assembly 70 measures the flow rate through the outlet of the ventilator and reports via sensing tubes 200 a pressure difference to a sensor connected to a processor 65, e.g. a CPU. The flow rate is then calculated/compensated and based on this calculation the ventilator will supply a predetermined/desired volume of gas to the patient.

Tubing system 90 includes an inhalation tube 92 and an exhalation tube 94. In the case of two limb ventilator the tubing system includes a junction/connector 96 connecting inhalation tube 92 to exhalation tube 94 and leading to the patient. Exhalation tube 94 further comprises an exhalation valve 80, and an external PEEP valve 88 downstream from exhalation valve 80. In other embodiments external PEEP valve 88 is upstream from exhalation valve 80 or alternatively a PEEP valve 88 can be in a combined assembly with exhalation valve 80.

Manifold assembly 40 also comprises an exhalation valve controller 84, which controls opening and closing of exhalation valve 80. In some embodiments, exhalation valve controller 84 includes one or more exhalation valve controllers. Exhalation valve 80 is connected to exhalation valve controller 84 via an exhalation valve control tube 81. It is noted that all flow paths shown within the manifold assembly 40—i.e. conduit 204 for supplying pressure to pneumatic solenoid valves, bleed conduit 49, and exhalation valve control tube 81—are not tubes but are tunnels created within the walls of the manifold as will be described herein below.

An oxygenator 26 is optionally also included within ventilator 10, and provides oxygen from an oxygen source that is added to the air supplied to turbine 22 when needed. A processor/CPU 65 is included within ventilator 10, and provides for operation of inspiratory valve controller 43, exhalation valve controller 84 and combinations thereof based on input from a user and/or an algorithm or multiple algorithms. Processor 65 can also set levels of oxygen enrichment if required), tidal volume, number of breaths per minute, maximum peak inspiratory pressure (PIP), and positive end expiratory pressure (PEEP). Any or all of these parameters may be fixed or adjustable.

Figure 8:
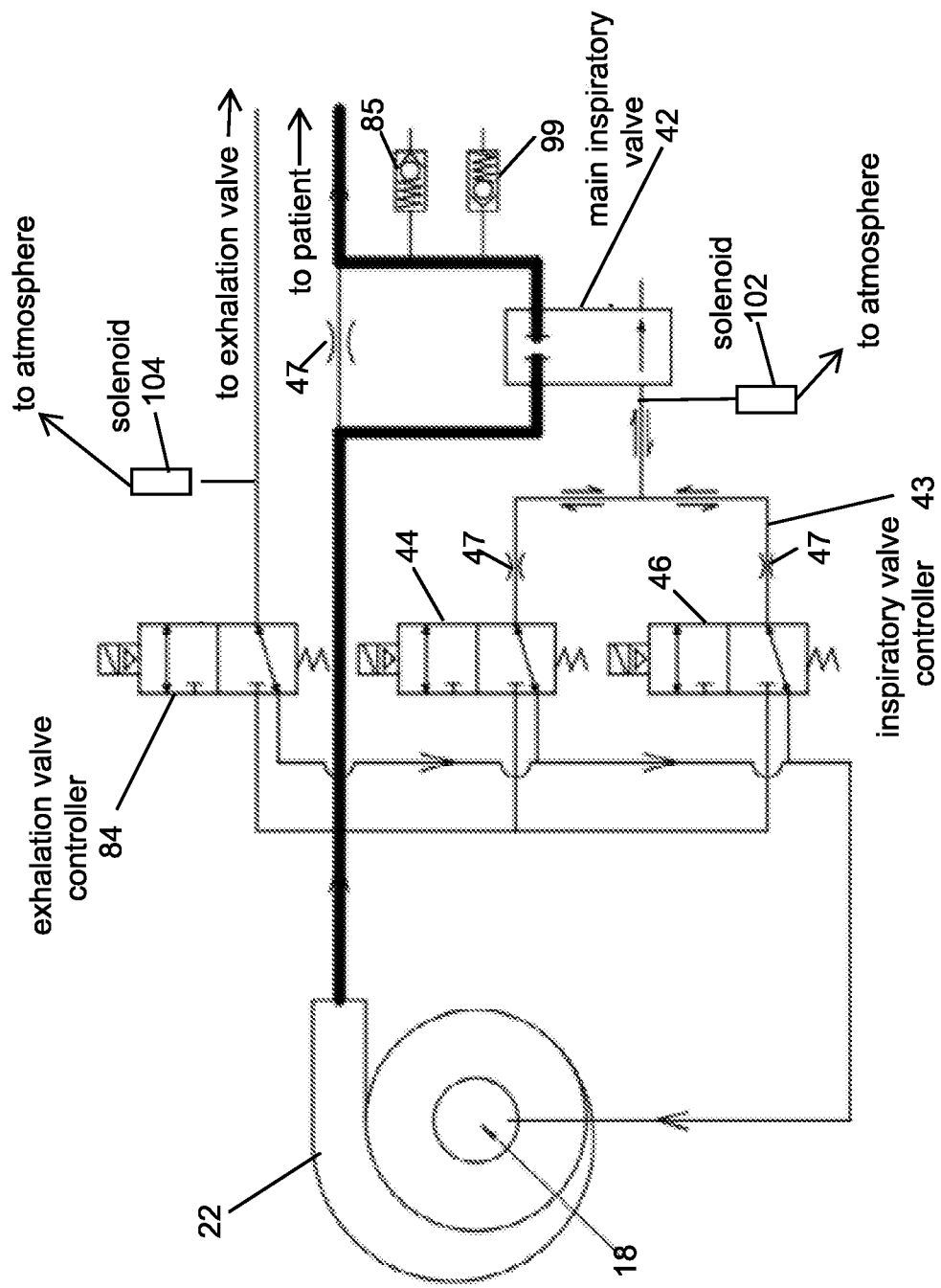
FIG. 8 schematically shows a pneumatic diagram illustration of the system of FIG. 1.

Optionally, ventilator 10 further includes an anti-asphyxia valve 85 (see FIG. 9) that bypasses the turbine in order to allow breathing if the turbine fails to function properly. It should be readily apparent that other features may be included within ventilator system 100, such as a safety valve 99 (see FIG. 9). Also a bypass solenoid that rapidly decreases the pressure to the patient 102, an additional solenoid disconnecting the PEEP valve in case there is continuous high pressure in the turbine 104 are shown in FIG. 8. Also, an additional solenoid that may connect to the system to control a nebulizer system enabling aerosol therapy to the patient. For simplicity, the solenoid and nebulizer system have not been included in the present figures.

FIG. 1B is a block diagram illustration of another embodiment of a ventilator system, in accordance with embodiments of the present invention. Ventilator system 100' comprises all components of ventilator system 100 of FIG. 1A. The difference between the two embodiments is that in ventilator system 100' the flow meter assembly 70 is located inside a housing of ventilator 10 instead of in tubing assembly 90.

In another embodiment, which is not shown in the figures, flow meter assembly 70 is located between the turbine 22 and the manifold assembly 40. Regardless of the position of flow meter assembly 70, during inspiration, pressurized gas (e.g., air) is sent via turbine 22 through manifold assembly 40 and into tubing system 90.

In some embodiments of the ventilator system, manifold assembly 40 may be integrated into turbine 22.

Figure 2A:
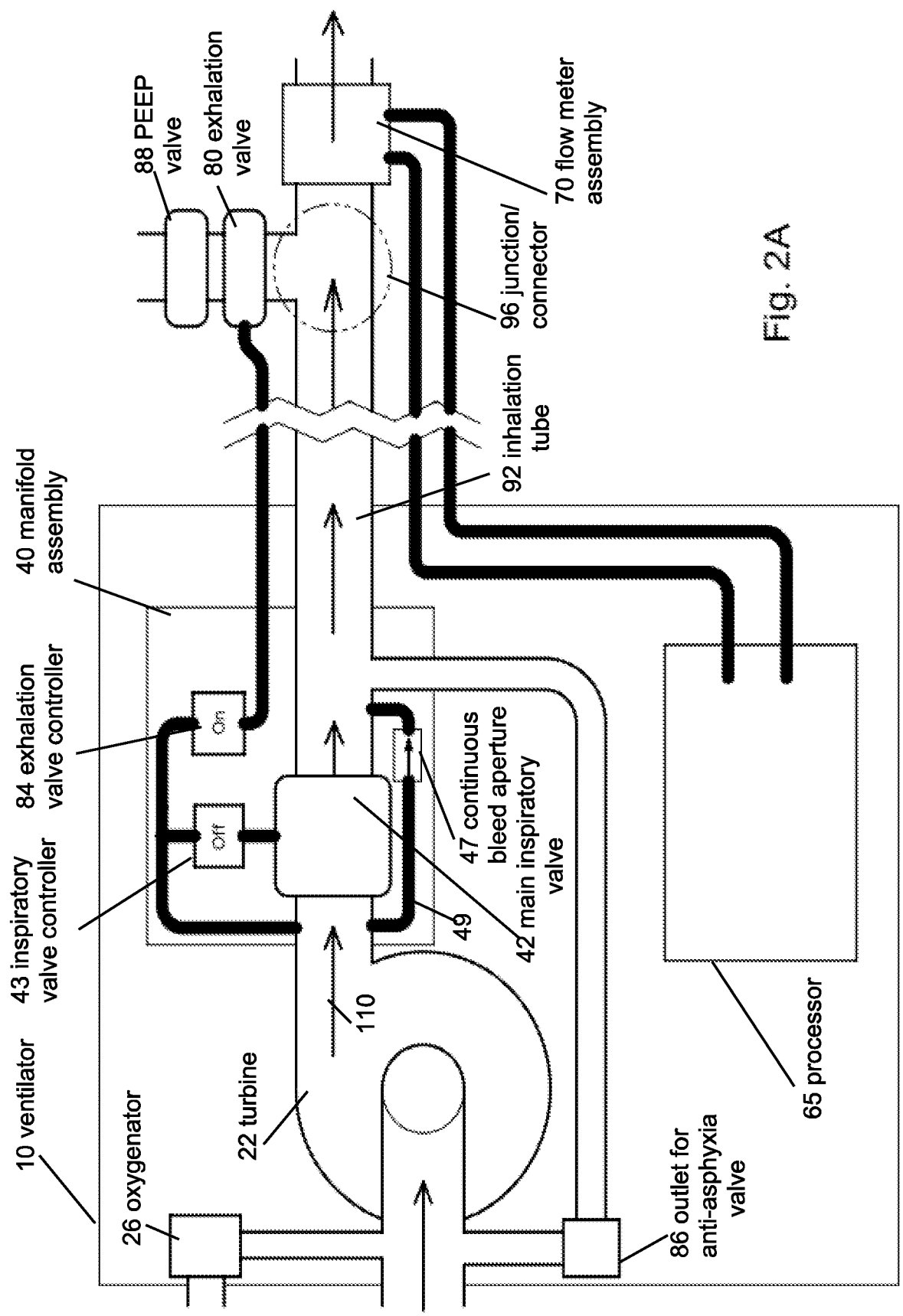
Figure 2B:
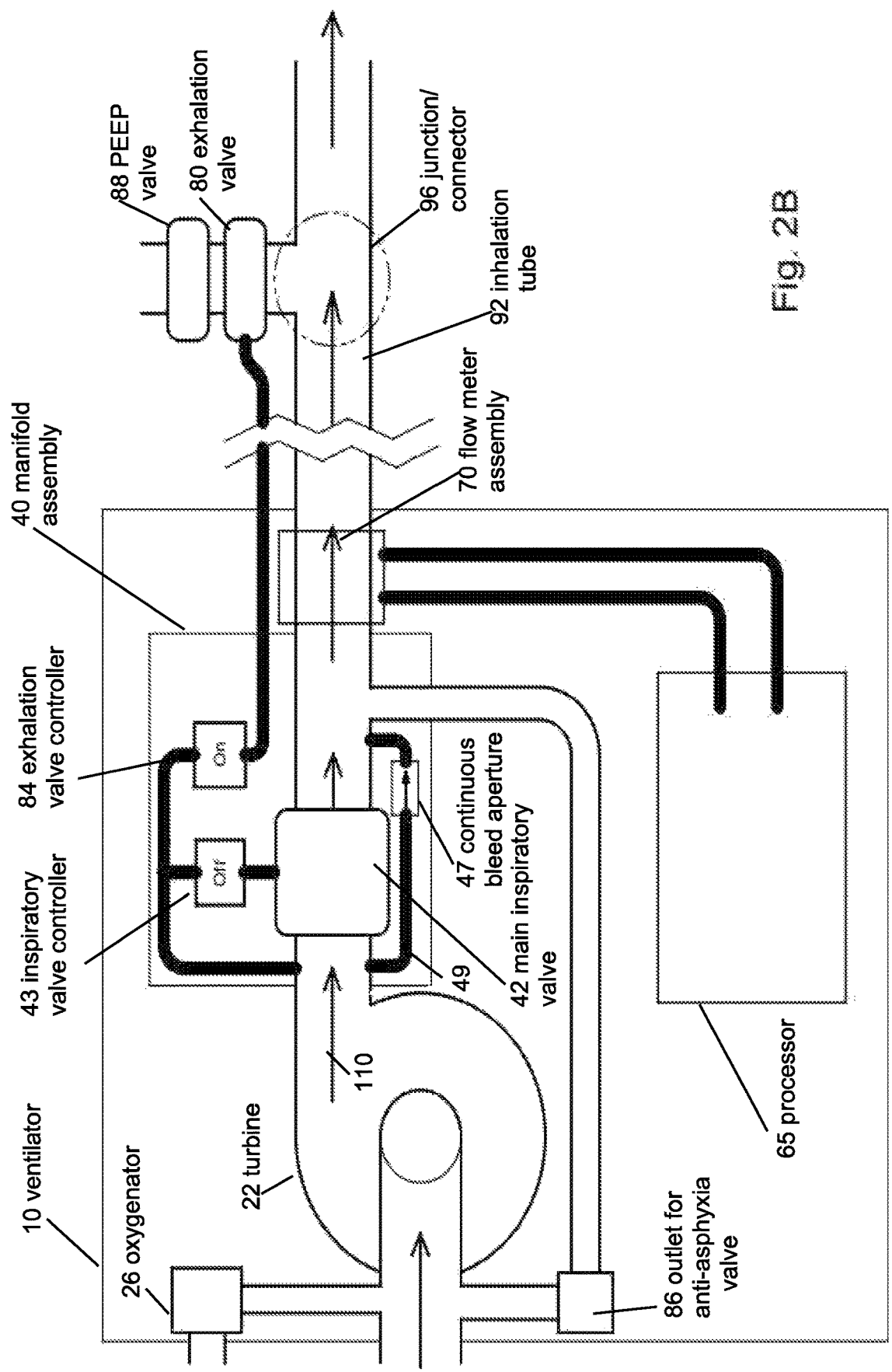
Figure 3A:
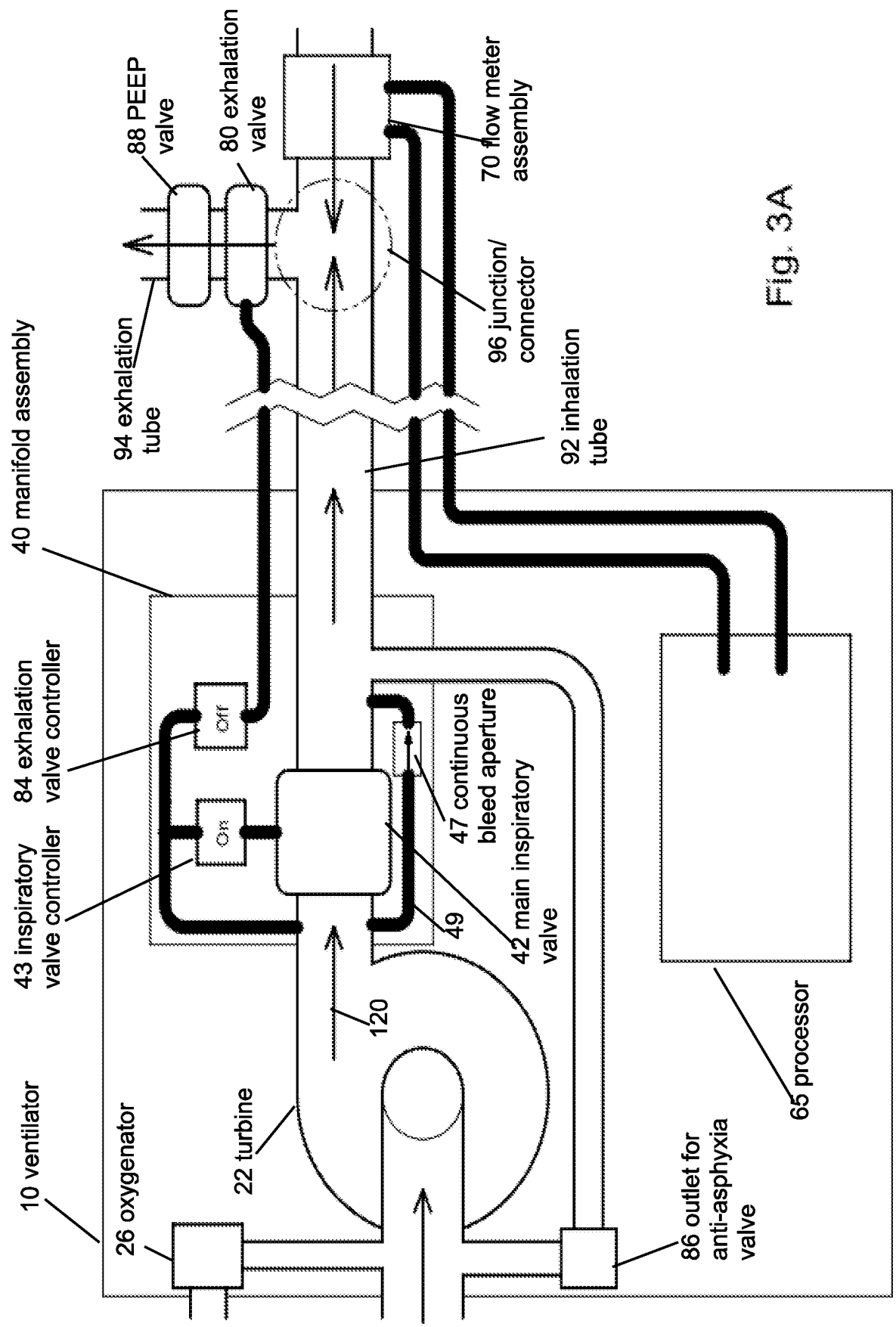
FIG. 3A and FIG. 3B schematically show block diagram illustrations of FIG. 1A and FIG. 1B respectively further depicting the flow of air during an expiratory cycle.
Figure 3B:
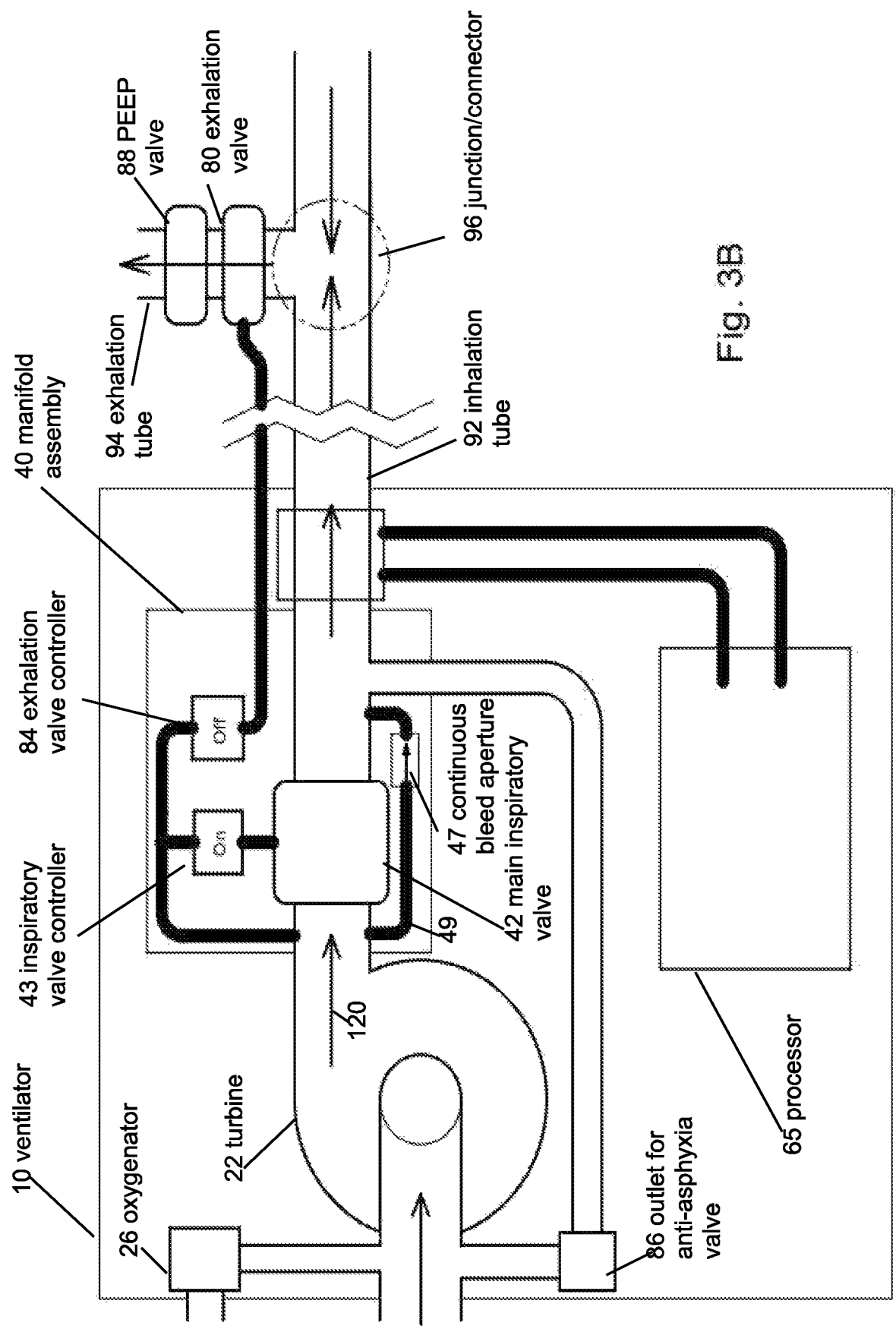

Reference is now made to FIG. 2A and FIG. 2B, which are block diagrams of FIG. 1A and FIG. 1B respectively depicting the flow of air during an inspiratory cycle, and to FIG. 3A and FIG. 3B, which are block diagrams of FIG. 1A and FIG. 1B respectively depicting the flow of air during an expiratory cycle. In both phases of the breathing cycle, ambient air is introduced into turbine 22. During the inspiratory cycle, as indicated in FIG. 2A and FIG. 2B by arrows 110, pressurized air from turbine 22 flows into both main inspiratory valve 42, which is open to air flow via operation of inspiratory valve controller 43, and into continuous bleed aperture 47, which in some embodiments is a small diameter hole that is always open to air flow via bleed conduit 49. In other embodiments, a proportional solenoid bleed valve is used that can be used to reduce or increase the size of the hole when and as needed. In embodiments of the invention continuous bleed aperture 47 can comprise both a small diameter hole and a proportional solenoid valve. Embodiments of the ventilator comprise an internally proportional valve responsible over the PEEP and not an external PEEP valve as in the ventilators described herein. In this case the solenoid bleed valve may be closed at times.

The volume of air flow through continuous bleed aperture 47 is small compared to the volume of air flow through main inspiratory valve 42. In some embodiments, the volume of air flow through continuous bleed aperture 47 ranges from 1% to 10% of the volume of air flow through main inspiratory valve 42. A typical (but not limiting) ratio of the free flow area of the two valves is 2 mm$^2$ to 400 mm$^2$. These two streams of air then combine, and flow through inhalation tube 92, past junction/connector 96 and to the patient. During this cycle, exhalation valve 80 is closed to air flow due to operation of exhalation valve controller 84. It should be readily apparent that both inspiratory valve controller 43 and exhalation valve controller 84 are activated by processor 65 such that opening and closing of main inspiratory valve 42 and exhalation valve 80 are well coordinated.

During the expiratory cycle, as indicated in FIG. 3A and FIG. 3B by arrows 120, pressurized air from turbine 22 is blocked from flowing through main inspiratory valve 42, due to operation of inspiratory valve controller 43, but does flow through continuous bleed aperture 47, which is open to air flow via bleed conduit 206. The volume of air flow through continuous bleed aperture 47 is relatively small. For example, continuous bleed aperture 47 may be a hole having a diameter of between 0.5 and 2.5 mm, which would result in a volume of between 2-20 liters per minute (1 pm) under free flow conditions, based on pressures of between 5-50 cmH$_2$O. Air flows from continuous bleed aperture 47 into inhalation tube 92, past junction/connector 96, and combines with exhaled air flowing from the patient into exhalation tube 94. During this cycle, exhalation valve 80 is open to air flow by means of exhalation valve controller 84. Air flowing from the patient and from continuous bleed aperture 47 flows through exhalation valve 80, into PEEP valve 88 and out into ambient air. It should be readily apparent that both inspiratory valve controller 43 and exhalation valve controller 84 are activated by processor 65 such that opening and closing of main inspiratory valve 42 and exhalation valve 80 are well coordinated.

It is a characterizing feature of the present invention that continuous bleed aperture 47 provides a continuous flow of air at all times while the turbine is operating. This design of continuous air flow provides several advantages over known ventilator systems. In known systems, if more air is needed by the patient, the revolutions per minute (RPM) of the turbine must be increased to accommodate the additional volumetric flow. This leads to an increase in energy consumption, resulting in greater overall power and size requirements.

In the present invention, since the exhalation valve is open, air passes continuously through the PEEP valve during the expiratory phase as long as the backpressure of the patient circuit and patient's lungs is higher than the preset PEEP value, which may be in the range 0-30 cmH$_2$O, but is in most cases 5 cmH$_2$O. The PEEP valve maintains a preset pressure during expiratory phase and the use of bleed aperture 47 eliminates the need for sensing, calculating or assessing any small leaks (e.g. through face mask, endotracheal tube, tube connectors etc. . . . ) in order to compensate for these flow leaks which, in the prior art are compensated for by increasing the RPM of the turbine or by partially closing the exhalation valve. These actions require both a large amount of energy and additional computational power.

Moreover, it is known that PEEP pressure must be provided in order to prevent lung collapse, and increase oxygen diffusion. That is, there must be a minimal air pressure in the lungs of the patient at all times. In known ventilator systems, the PEEP pressure in turbine operated ventilators is provided by several possible methods: A) using a constant PEEP valve and accelerating and decelerating the turbine during the various breath cycles; B) controlling the pressure line by a proportional valve or restrictor connected to the turbine outlet and creating a pneumatic bypass between outlet and inlet of the turbine, in order to allow fast reduction and increase in pressure per the required breath cycle (inspiration/expiration); C) directly blocking the inspiratory path from the turbine to the patient, thus creating expiratory and inspiratory cycles.

The more constant the RPM of the turbine, the more electrically efficient the ventilator is; therefore, there is a great advantage in preventing the RPM fluctuations due to leak compensations or sudden increase of flow to the patient. In the ventilator systems 100 and 100' of FIG. 1A and FIG. 1B, continuous bleed aperture 47 provides a constant PEEP while preventing RPM fluctuations by providing a small controllable bleeding of gas from the patient circuit.

As used herein the term "patient circuit" refers to a circuit e.g. tubes transferring gas to and from the patient.

At the beginning of the expiratory phase there is a quick passage of flow (usually at a flow rate of more than twice the flow rate during inspiratory phase, e.g. 80 lpm in comparison to 40 lpm, which creates a sharp decrease in pressure that allows the patient to exhale. After the expiratory phase the ventilator 100 regains the PEEP by closing the exhalation valve 80. When this happens it is possible that the pressure will drop sharply, e.g. 20 cmH$_2$O in a few hundreds of milliseconds. When this occurs the patient's lungs and the patient circuit may exhibit a lowered value of pressure by several cmH$_2$O and can sometimes drop under the PEEP value which is constant and usually in the order of magnitude of 5 cmH$_2$O. The pressure may be regained by the continuous bleed aperture 47 and by controlling the closure of the main valve 42.

Finally, the use of continuous bleed aperture 47 prevents accumulation of CO$_2$ since there is continuous dilution of dead space. Moreover, the use of an external PEEP valve helps keep pressure constant in the airways since it acts as a safety valve that, no matter what pressure there is in the ventilator, while air flows through the ventilator the PEEP valve will open only starting at 5 cmH$_2$O.

Figure 5:
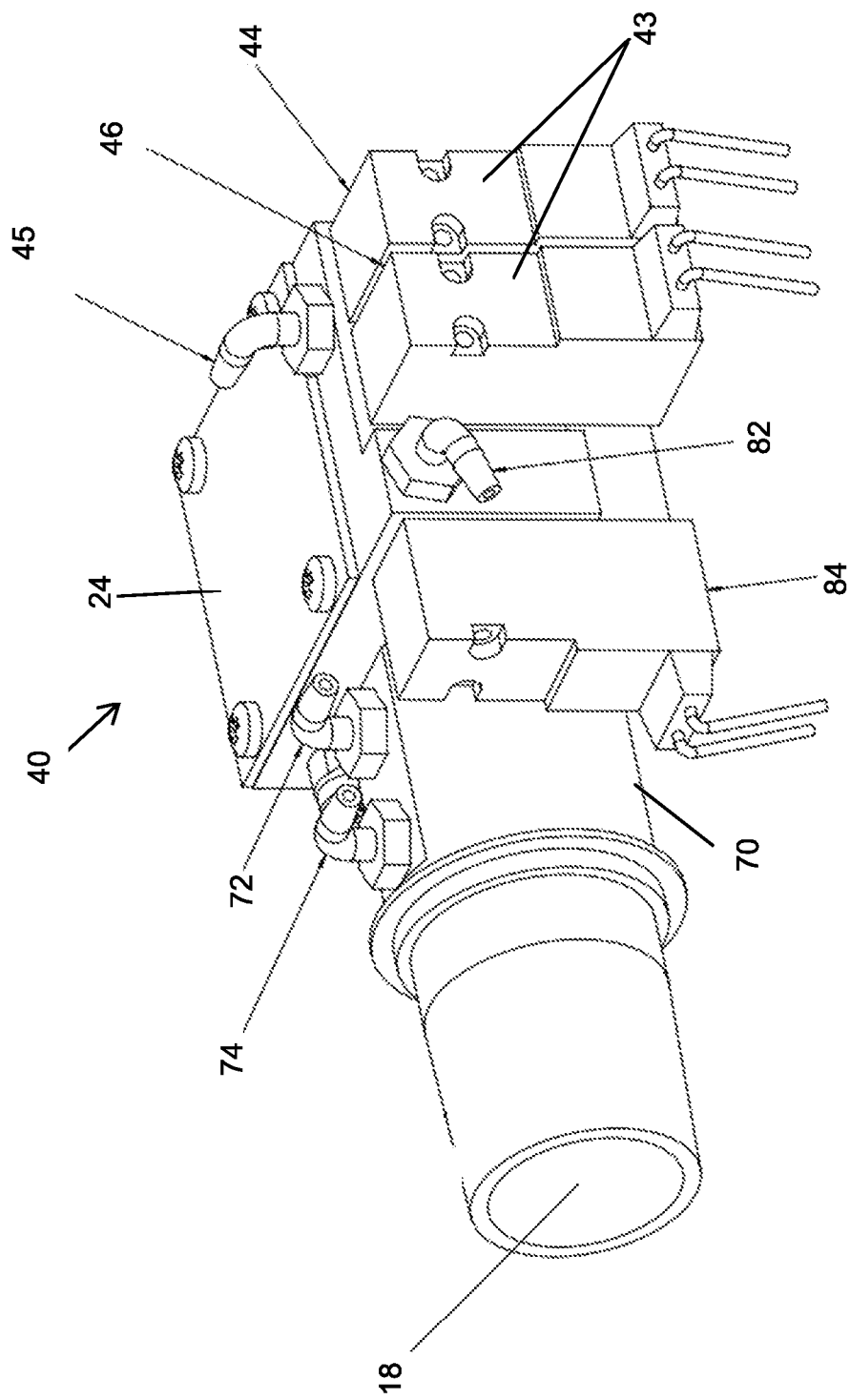

Reference is now made to FIGS. 4 and 5, which are perspective illustrations of manifold assembly 40 and flow meter assembly 70 shown from different angles. A characterizing feature of the present invention is that manifold assembly 40 comprises a manifold block 24, which is configured to hold the main operating components of ventilator 10, including main inspiratory valve 42, continuous bleed aperture 47, and most or all of the tubes and wires needed for operating manifold assembly 40 within the interior of manifold block 24 and inspiratory valve controller 43 and exhalation valve controller 84 attached to the exterior surface of manifold block 24.

Manifold block 24 is a compact unit, which has a volume in the range of 15 to 100 cm³. In one embodiment the manifold block has dimensions of approximately 40 mm×35 mm×30 mm. The use of manifold block 24 allows for the overall size and weight of ventilator 10 to be greatly minimized. In typical embodiments, the weight of ventilator 10 is in a range of 0.6-1.6 Kg, for example, which is a significant improvement over currently known portable turbine operated ventilators, which are much larger and which generally weigh no less than 4.5 Kg. Moreover, the use of manifold block 24 allows for all of the pneumatic control elements to be concentrated near blower 22, thus eliminating the need for tubes, conduits and channels by creating them in the walls of the manifold block.

Manifold block 24 has a manifold block proximal end 28 having a blower input tube 36 connected to blower 22; a manifold block distal end 30, which in this embodiment is connected via outlet 18 of flow meter assembly 70 to the inhalation tube 92; a manifold block anterior portion 32; a manifold block posterior portion 34; a manifold block superior portion 33; and a manifold block inferior portion 35. These designations are for descriptive purpose so that the geometric relationship between elements within manifold block 24 may be understood, but should not be regarded as limiting.

Blower input tube 36 may be, for example, a connector having a round shape or any other suitable shape for accepting a blower output. Air flow is provided from blower 22 through blower input tube 36 at manifold block proximal end 28 and continues through to manifold assembly distal end 30 and out through outlet 18 to the patient. Shown attached to the exterior of manifold block 24 are inspiratory valve controller 43, which in this case is comprised of two solenoids 44 and 46, and exhalation valve controller 84. Also seen in the figures are flow meter assembly 70, an outlet 86 for an anti-asphyxia valve, solenoid valve exhaust 45, exhalation valve port 82, and flow meter ports 72 and 74.

Figure 6:
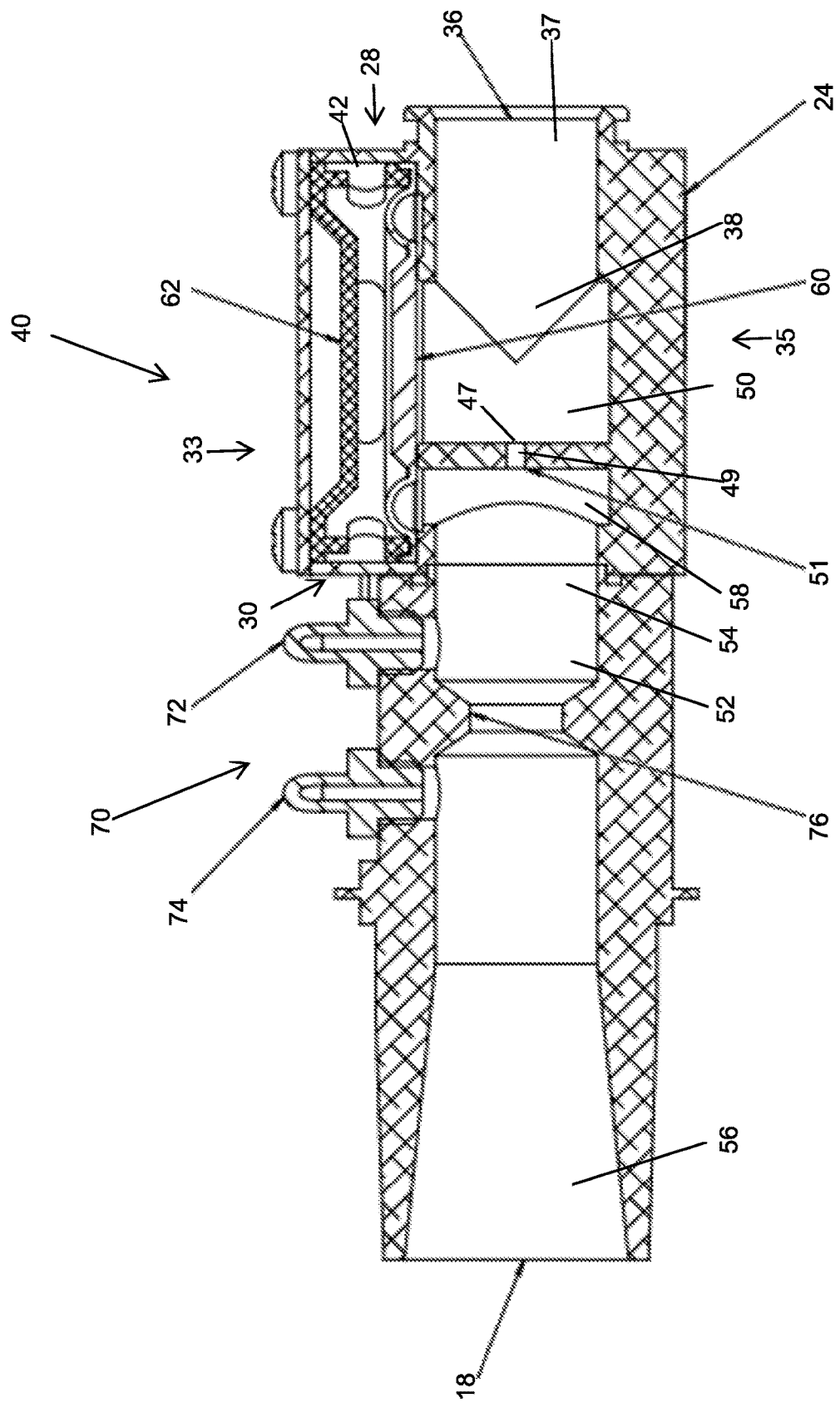
FIGS. 6 and 7 schematically show cross-sectional illustrations of the manifold block of FIGS. 4 and 5 respectively.
Figure 7:
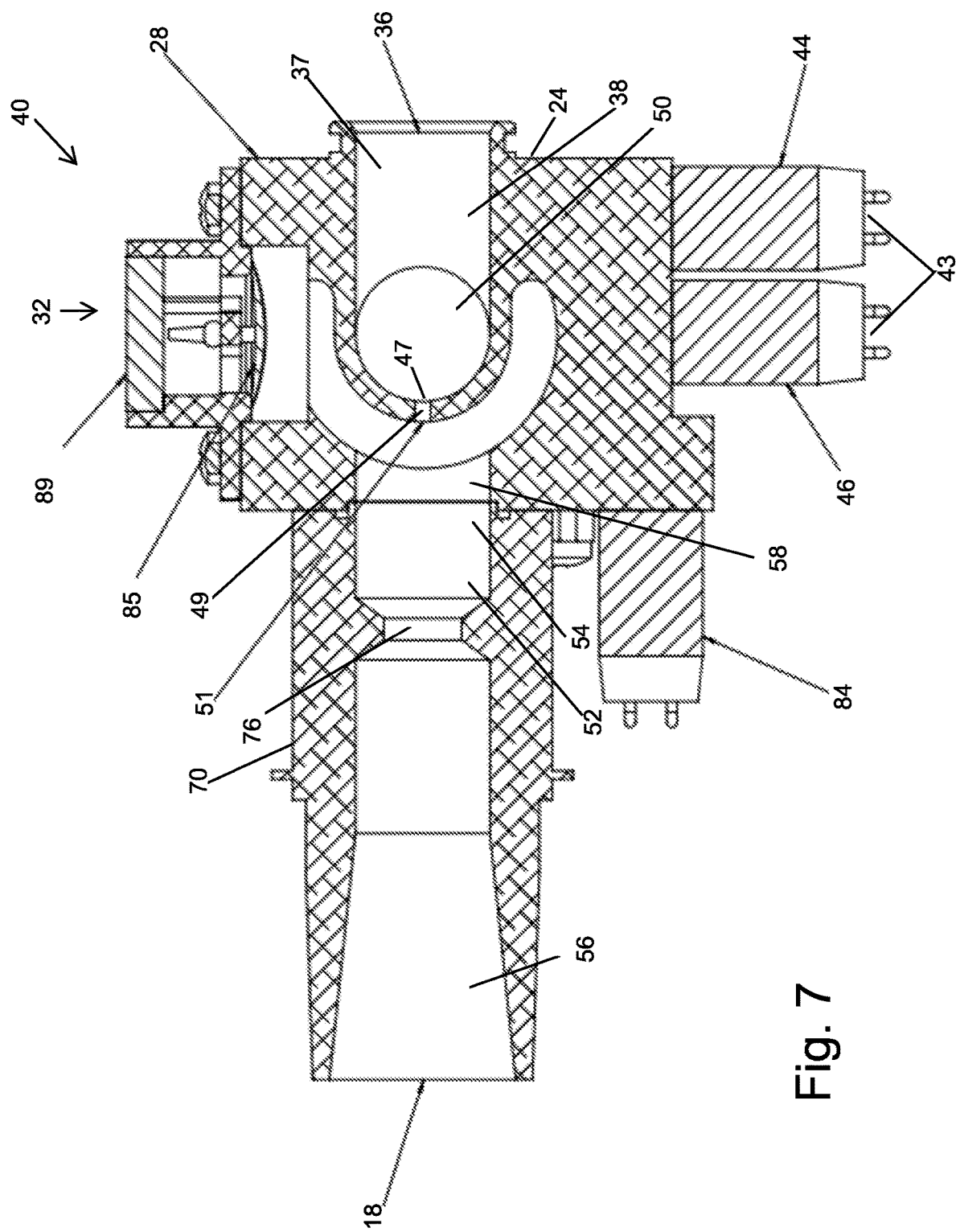

Reference is now made to FIGS. 6 and 7, which are cross-sectional illustrations of manifold block 24 depicting a manifold assembly 40 and a flow meter assembly 70 through which air passes as air flow progresses from manifold block proximal end 28 to flow meter assembly outlet 18. FIG. 6 shows a section as viewed posteriorly across a longitudinal cut from manifold block proximal end 28 to outlet 18. FIG. 7 shows a section as viewed anteriorly across a longitudinal cut from manifold block proximal end 28 to outlet 18. Manifold assembly 40 includes a main inspiratory valve 42 which is controlled by main inspiratory controller 43. Main inspiratory controller 43 may comprise one or multiple solenoids for example. In the embodiment shown herein, main inspiratory controller 43 includes a first solenoid 44 and a second solenoid 46, as seen in FIGS. 4, 5, and 7. Main inspiratory valve 42 is configured to be open (off) during an inspiration portion of the breathing cycle and closed (on) during an expiration portion of the breathing cycle. Main inspiratory controller 43 further includes a valve exhaust 45 (shown in FIGS. 4 and 5), which may be connected to blower input tube 36 to minimize loss of energy. Valve exhaust 45 provides venting of internal pressure within main inspiratory valve 42, to ensure that oxygen is not released into ventilator 10. Valve exhaust 45 is connected to the inlet so as not to exceed a predetermined oxygen concentration inside the ventilator.

The use of two or more controllers, such as first solenoid 44 and second solenoid 46, provides a large variety of control options for speed and duration of opening and closing of main inspiratory valve 42. In the example shown herein, wherein two solenoids are used, each solenoid may be programmed with a separate timing mechanism, wherein, for example, one solenoid may open rapidly and the other may open slowly. Thus use of two such solenoids, with different speeds, provides three speed options. For example, if first solenoid 44 has a first speed and second solenoid 46 has a second speed, inspiration may occur at the first speed using only first solenoid 44, at the second speed using only second solenoid 46, or at a third speed by using both first and second solenoids 44 and 46. The number of possible speeds may be further increased by adding additional solenoids to main inspiratory controller 43. The variety of options may be further increased by one or more of the solenoids having proportional control, rather than discrete control. One particular use of this configuration is in a case where a sudden inhalation is required. Thus, one of the solenoids can be programmed to have a very fast speed for such instances. The use of multiple valves provides control over the slope of the pressure curve during initiation of breathing. In a non-limiting example a breath may be detected by means of pressure change (inspiratory attempt is characterized by negative pressure created in the patient's lungs), flow change or even electrical signal detected in the patient's muscles. The detection time may range between 1-50 milliseconds (depending on the method) and solenoid activation (initiation of flow) may vary between 1-50 msec. A fast response would be considered if flow onset begins less than 50 msec after detection of breath effort.

Blower input tube 36, which is in fluid communication with blower 22, has a blower input tube proximal end 37 and blower input tube distal end 38. At blower input tube distal end 38, an inspiratory valve first connector 50 is connected to blower input tube 36 and to main inspiratory valve 42. Inspiratory valve first connector 50 is positioned substantially perpendicular to blower input tube 36 such that air flows in a proximal to distal direction from blower input tube 36 into inspiratory valve first connector 50 and in an inferior to superior direction from inspiratory valve first connector 50 to main inspiratory valve 42. In addition, inspiratory valve first connector 50 includes thereon a continuous bleed aperture 47 leading into a continuous bleed conduit 49. Continuous bleed aperture 47 is an opening which provides a small amount of air flow continuously from inspiratory valve first connector 50 to continuous bleed conduit 49, both during the inspiration portion of the breathing cycle and during the expiration portion of the breathing cycle. In embodiments of the present invention, main inspiratory valve 42 is positioned in a superior position relative to continuous bleed conduit 49 and to blower input tube 36. It should be readily apparent that other positions are possible as well. Both main inspiratory valve 42 and continuous bleed conduit 49 are in fluid communication with an inspiratory air tube 52 via an inspiratory valve second connector 58. Similar to inspiratory valve first connector 50, inspiratory valve second connector 58 is positioned substantially perpendicular to inspiratory air tube 52 such that air flows in a superior to inferior direction from main inspiratory valve 42 to inspiratory valve second connector 58 and in a proximal to distal direction from inspiratory valve second connector 58 to inspiratory air tube 52. In addition, inspiratory valve second connector 58 includes thereon a second continuous bleed aperture 51 leading from continuous bleed conduit 49 into inspiratory air tube 52.

Inspiratory air tube 52 has an inspiratory air tube proximal end 54 and an inspiratory air tube distal end 56. When open (i.e. during an inspiratory phase), air flows from main inspiratory valve 42 through inspiratory valve second connector 58 into inspiratory air tube 52 at inspiratory air tube proximal end 54. Air also flows from continuous bleed conduit 49 via inspiratory valve second connector 58 into inspiratory air tube 52 at inspiratory air tube proximal end 54 at all times that air is provided to blower input tube 36 via blower 22. That is, flow of air through continuous bleed conduit 49 is not dependent on the phase of the cycle, and thus occurs during both the inspiratory and expiratory phases. A diameter of continuous bleed conduit 49 is typically in a range of 0.5-2.5 mm, so that the continuous bleed is of a relatively small volume. During the inspiratory cycle, when air is flowing from main inspiratory valve 42 into inspiratory air tube 52, the air which flows from continuous bleed conduit 49 combines with the air from main inspiratory valve 42 and is negligible with respect to the total amount of air flow. During the expiratory cycle, when air is not flowing from main inspiratory valve 42 into inspiratory air tube 52, the air which flows from continuous bleed conduit 49 continues along the flow path alone. Inspiratory air tube distal end 56 leads to outlet 18, such that air flowing therein is provided to the patient, as will be described further herein below.

In embodiments of the present invention, a flow meter assembly 70 is included within inspiratory air tube 52. It should be readily apparent that the position of flow meter assembly 70 is not limited to the position shown and described herein, and may be placed at other strategic locations along the inspiratory air flow path. In the embodiment shown herein, flow meter assembly includes a first flow meter port 72 and a second flow meter port 74. In between first flow meter port 72 and second flow meter port 74, inspiratory air tube 52 has a narrowed air tube portion 76. Narrowed air tube portion 76 has a diameter of between 3-8 mm, which is much smaller than the diameter at the other portions of inspiratory air tube 52, which is in a range of 14 mm. This narrowing causes a pressure increase, i.e. a pressure difference between two sides of the orifice, which is then used to extract and calculate the volumetric flow passing through the narrow channel. Flow meter assembly 70 in the embodiment shown herein is a Venturi flow meter and may be, for example, a flow meter such as described in U.S. Pat. No. 6,802,225. This type of flow meter is very small yet accurate. However, flow meter assembly 70 may be any suitable flow meter such as, for example, a hot wire anemometer, an impeller flow meter, an ultrasonic, an optical, or any other type of flow meter known in the art that can be suitably adapted to measure flow of air in the ventilator system.

Manifold block 24 further includes an exhalation valve controller 84, connected to an exhalation valve port 82 (shown in FIGS. 4 and 5). Exhalation valve port 82 leads to an exhalation tube 81, which leads to an exhalation valve 80, both located outside of ventilator 10 and depicted schematically in FIG. 1, for example. As shown in FIGS. 4 and 5, exhalation valve controller 84 and exhalation valve port 82 are positioned on manifold block 24, distal to first and second solenoids 44 and 46. The positions of exhalation valve controller 84 and exhalation valve port 82 are not limited to the ones shown herein. Exhalation valve controller 84 may be, for example, a solenoid and in some embodiments may also have proportional control as described herein above. Exhalation valve controller 84 is configured to open exhalation valve 80 during an expiratory phase of the cycle and to close exhalation valve 80 during an inspiratory phase of the cycle.

Manifold block 24 further includes an anti-asphyxia valve 85, which allows the patient to breathe in circumstances in which blower 22 stops working. As shown in FIG. 4, anti-asphyxia valve outlet 86 is positioned in anterior portion 32 of manifold block 24. However, it should be readily apparent that other positions are possible for anti-asphyxia valve 85. Manifold block 24 may further include a safety (i.e. high pressure) valve 99 (see FIG. 8) as well in order to prevent barotrauma and other lung injuries. In embodiments of the present invention, safety valve 99 may be a hardware protection mechanism (such as limit of RPM, pressure or other software implementations) used to limit the pressure generated in the blower. In FIG. 7 is seen a removable top plate 89 that covers the anterior portion of the manifold block 24.

Reference is now made to FIG. 8, which is a pneumatic diagram illustration of the system 100, showing the air flow paths during an inspiratory phase and during an expiratory phase of the breathing cycle. Turbine 22 is configured to receive ambient air and optionally oxygenated air via air/$O_2$ inlet 18. Turbine 22 provides air to blower input tube 36. If either or both of first solenoid 44 and second solenoid 46 is open, air flows through the open solenoid (or through both open solenoids) to main inspiratory valve 42 and into the inhalation tube leading to the patient. In any case, whether or not first or second solenoid 44 or 46 is open, a small amount of air flows through continuous bleed aperture 47 and into the inhalation tube leading to the patient. Gas flowing out from main inspiratory valve 42 may be sent back to turbine 22. During the expiratory phase, exhalation valve controller 84 adjusts the pressure in the control line to open exhalation valve 80 located on the exhalation tube. Gas flowing out of exhalation valve controller 84 may be sent back to blower 22.

Figure 9A:
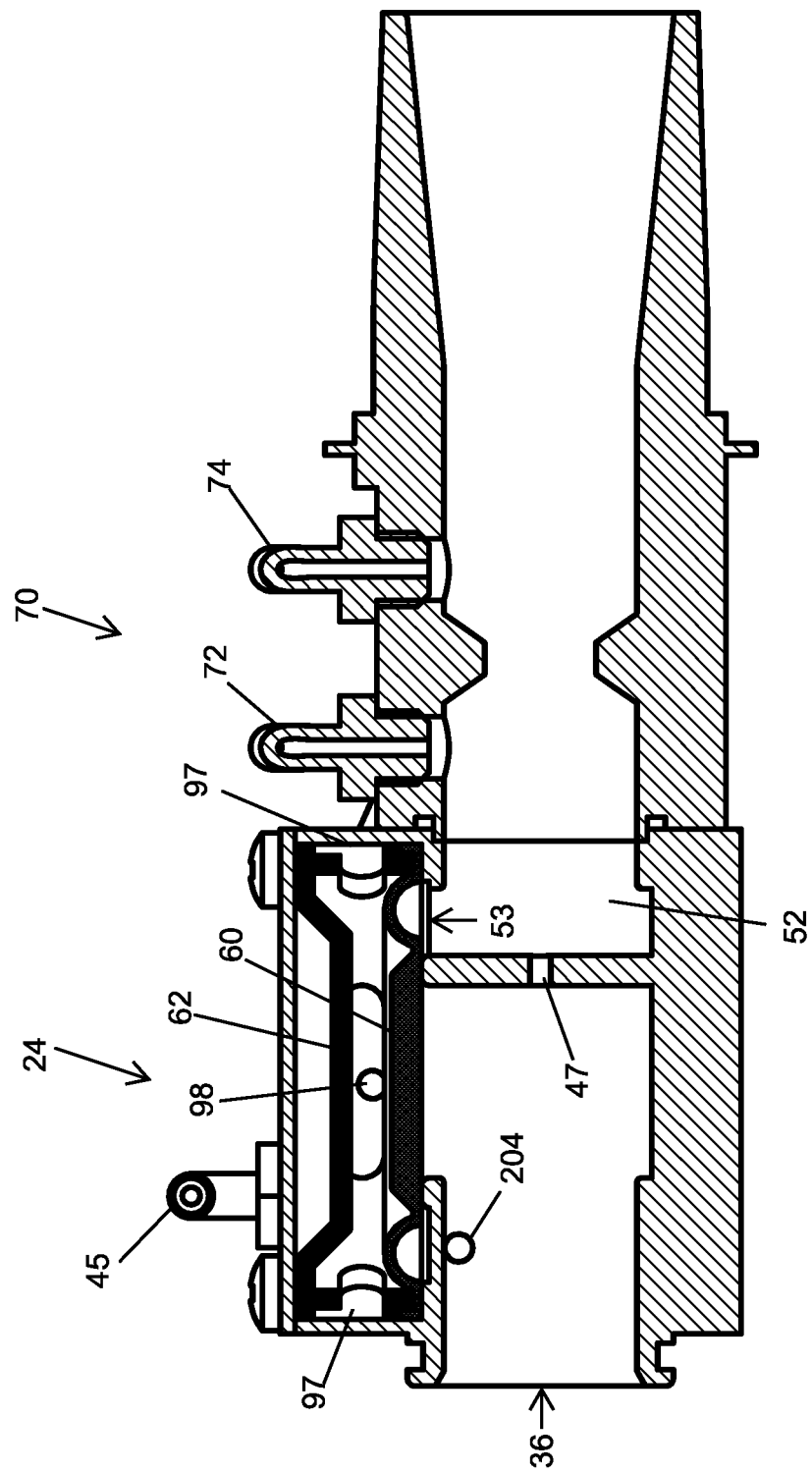
FIG. 9A schematically shows a partially cut section showing an embodiment of a main inspiratory valve.
Figure 9B:
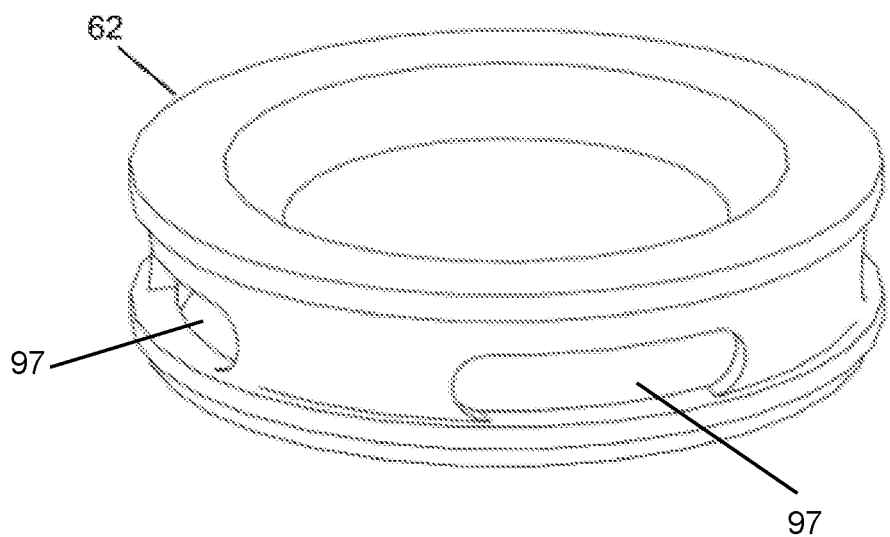
FIG. 9B schematically shows a perspective illustration of a portion of a spacer used to hold the diaphragm in position in an embodiment of a main inspiratory valve.

Reference is now made to FIG. 9A, which is a partially cut section showing an embodiment of a main inspiratory valve 42 in manifold 24, and to FIG. 9B, which is a perspective view of a spacer 62 placed above the diaphragm and the cover of the main inspiratory valve 42.

Main inspiratory valve 42 works via opening and closing of a diaphragm 60. Diaphragm 60 is comprised of a flexible material, for example silicone, and is positioned over opening 53 leading into inspiratory valve first connector 50. Diaphragm 60 is configured to move from a superior to an inferior position, wherein in a superior position, opening 53 is open to air flow and in an inferior position, diaphragm 60 covers opening 53, thus blocking air flow into inspiratory air tube 52. Movement of diaphragm 60 into a superior or inferior position (i.e., opening and closing of main inspiratory valve 42) is controlled by one or both of first and second solenoids 44 and 46 via a channel whose opening 98 is seen above diaphragm 60. Seen in the figure are the entrance to conduit 204 for supplying pressure to pneumatic solenoid valves and solenoid valve exhaust 45.

In some embodiments of the invention, diaphragm 60 is positioned below a spacer 62, which restricts the degree to which diaphragm 60 can move in the superior direction. Spacer 62 may have vent windows 97 to allow gas passage to and from diaphragm 60. The spacer 62 shown in view in FIG. 9B is just one of many possible ways that can be used to hold the diaphragm in position over opening 53.

Figure 10:
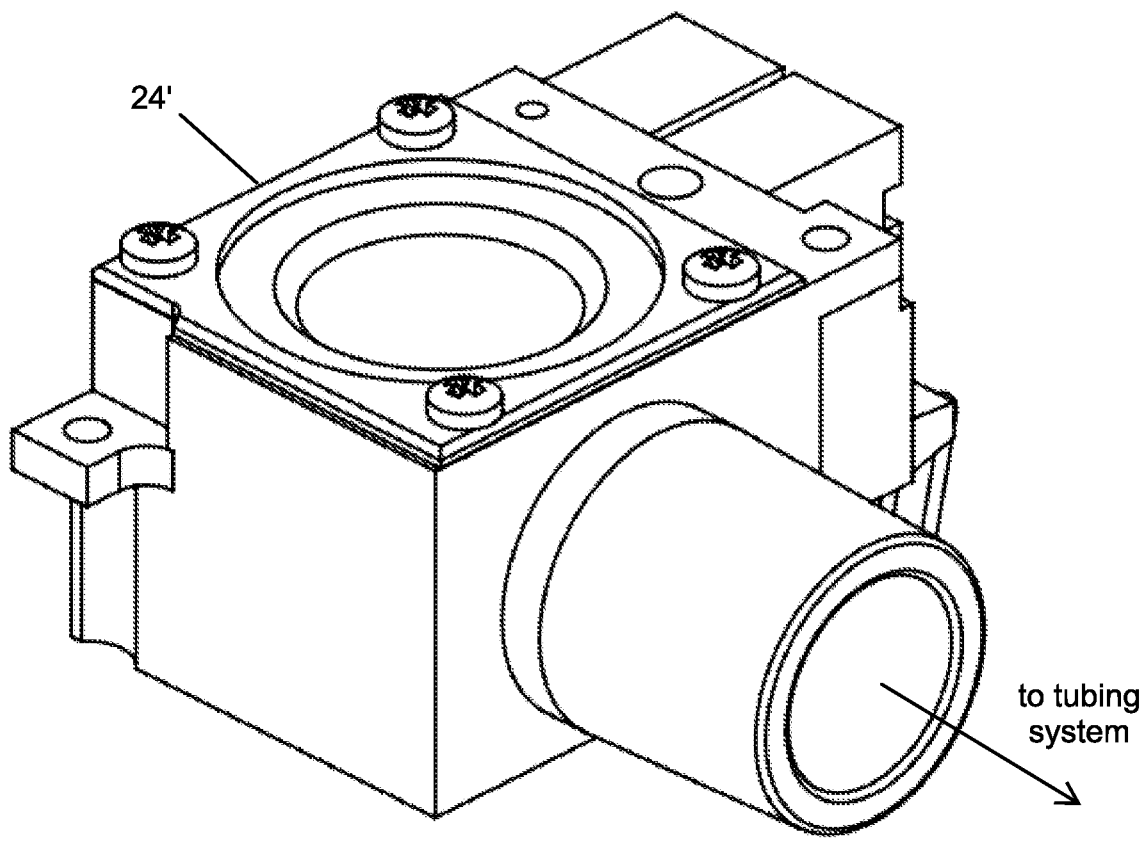
FIG. 10 schematically shows a perspective illustration of an embodiment of a manifold block that is not connected to a flow meter.

FIG. 10 schematically shows a perspective illustration of an embodiment of a manifold block 24' that is not connected to a flow meter. In this embodiment the flow meter is incorporated into the tubing system outside of the ventilator. This allows the weight and size of the ventilator to be reduced when compared to ventilators comprising with flow meter attached to the manifold block as in FIGS. 4-7.

Although embodiments of the invention have been described by way of illustration, it will be understood that the invention may be carried out with many variations, modifications, and adaptations, without exceeding the scope of the claims.

The invention claimed is:

1. A portable positive pressure ventilator system for providing respiratory support to a patient, the ventilator system comprised of:
   (a) a ventilator comprising a source of pressurized air,
   (b) a manifold assembly; and
   (c) a tubing system connected to the ventilator and to the patient;
   wherein,
   (A) the manifold assembly comprises a manifold block, which holds main operating components of the ventilator and a continuous bleed aperture;
   (B) at all times while the source of pressurized air is operating to provide pressurized air to the ventilator, the ventilator provides a continuous flow of air via the continuous bleed aperture to the tubing system;
   the portable positive pressure ventilator system characterized in that:
   I) the manifold block comprises:
      a) three chambers formed within an interior of the manifold block, wherein:
         i) a first chamber comprises a diaphragm of a main inspiratory valve;
         ii) a second chamber is configured as an inspiratory valve first connector, which is a chamber into which gas from the source of pressurized air enters the manifold block; and
         iii) a third chamber is configured as an inspiratory valve second connector, which is a chamber connected on a distal end of the third chamber to the tubing system that leads to the patient;
      b) a wall that separates the second chamber from the third chamber;
      c) a small diameter hole that passes through the wall;
      d) an outlet for an anti-asphyxia valve and all flow paths needed for fluidly connecting and operating the main operating components of the ventilator are created within walls of the manifold block;
      e) an inspiratory valve controller and an exhalation valve controller attached to the exterior surfaces of the manifold block; and
      f) an opening leading from the first chamber into the second chamber, which is opened and closed by the diaphragm of the main inspiratory valve when the main inspiratory valve is activated by the inspiratory valve controller;
   II) the small diameter hole that passes through the wall is configured to be the continuous bleed aperture.

2. The ventilator system of claim 1, comprising a flow meter assembly, which is located at one of the following locations in the system: within the ventilator housing between the source of pressurized air and the manifold block; within a ventilator housing between the manifold block and the tubing system; and on the tubing system.

3. The ventilator system of claim 1, wherein the tubing system includes, in the case of a one limb ventilator, a single tube that function as both an inhalation tube and an exhalation tube; and, in the case of a two limb ventilator, a junction or connector connecting an inhalation tube to an exhalation tube and leading to the patient.

4. The ventilator system of claim 3, wherein the exhalation tube comprises an exhalation valve.

5. The ventilator system of claim 1, comprising a PEEP valve located at one of the following places in the system: downstream from an exhalation valve, upstream from the exhalation valve; and in a combined assembly with the exhalation valve.

6. The ventilator system of claim 5, wherein the ventilator comprises at least one of: an oxygenator; an anti-asphyxia valve; a safety valve; a bypass solenoid valve that rapidly decreases the pressure to the patient; and a solenoid valve disconnecting the PEEP valve in case there is continuous high pressure in the source of pressurized air.

7. The ventilator system of claim 1, wherein the ventilator comprises a processor.

8. The ventilator system of claim 7, wherein the ventilator system comprises a processor configured to control solenoid valves in the ventilator system to:
   (a) provide for operation of the inspiratory valve controller and the exhalation valve controller based on input from a user or an algorithm or multiple algorithms;
   (b) to set levels of oxygen enrichment; and
   (c) to set levels of tidal volume, number of breaths per minute, maximum peak inspiratory pressure (PIP), and positive end expiratory pressure (PEEP),wherein a level of at least one of oxygen enrichment, tidal volume, number of breaths per minute, PIP, or PEEP is fixed or adjustable.

9. The ventilator system of claim 1, wherein the continuous bleed aperture is comprised of both the small diameter hole and a proportional solenoid bleed valve.

10. The ventilator system of claim 1, wherein a volume of air flow through the continuous bleed aperture ranges from 1% to 10% of a volume of air flow through the main inspiratory valve.

11. The ventilator system of claim 1, wherein a ratio of free flow area of the continuous bleed aperture to free flow area of the main inspiratory valve is 2 $mm^2$ to 400 $mm^2$.

12. The ventilator system of claim 1, wherein the continuous bleed aperture has a diameter of between 0.5 and 2.5 mm, which results in a volumetric flow rate of between 2 and 20 liters per minute under free flow conditions, based on pressures of between 5 and 50 $cmH_2O$.

13. The ventilator system of claim 4, wherein during an inspiratory cycle the exhalation valve is closed to air flow and a stream of air flowing through the main inspiratory valve combines with a stream of air flowing through the continuous bleed aperture and the combined streams flow through the inhalation tube past the junction or connector to the patient.

14. The ventilator system of claim 4, wherein during an expiratory cycle the main inspiratory valve is closed to air flow and a stream of air flowing through the continuous bleed aperture flows into the inhalation tube past the junction or connector and combines with a stream of exhaled air flowing from the patient into the exhalation tube and the combined streams flow through the exhalation valve and a PEEP valve out into ambient air.

15. The ventilator system of claim 1, wherein the manifold block is integrated into the source of pressurized air.

16. The ventilator system of claim 1, wherein the main inspiratory valve is a diaphragm valve comprising:
   a) the second chamber;
   b) the third chamber; and
   c) the diaphragm.

17. A manifold block for use in a portable positive pressure ventilator system comprising a ventilator for providing respiratory support to a patient, the manifold block comprising:

a) three chambers that are formed within its interior, wherein:
  i) a first chamber comprises a diaphragm of a main inspiratory valve;
  ii) a second chamber is configured as an inspiratory valve first connector, which is a chamber into which gas from the source of pressurized air enters the manifold block; and
  iii) a third chamber is configured as an inspiratory valve second connector, which is a chamber connected on a proximal end of the third chamber to a tubing system that leads to the patient;
b) a wall that separates the second chamber from the third chamber;
c) a small diameter hole that passes through the wall;
d) an outlet for an anti-asphyxia valve and all flow paths needed for fluidly connecting and operating main operating components of the ventilator created within walls of the manifold block;
e) an opening leading from the first chamber into the second chamber, which is opened and closed by the diaphragm of the main inspiratory valve when the main inspiratory valve is activated by an inspiratory valve controller;
wherein, the small diameter hole that passes through the wall is configured to be a continuous bleed aperture.

18. The manifold block of claim 17, comprising the inspiratory valve controller and an exhalation valve controller attached to its exterior surfaces.

19. The manifold block of claim 17, wherein the main inspiratory valve is a diaphragm valve comprising:
a) the second chamber;
b) the third chamber; and
c) the diaphragm.

20. A method of maintaining a predetermined value of positive end expiratory pressure (PEEP) within a respiratory passageway of a patient connected to the positive pressure ventilator system of claim 1, the ventilator system comprised of: the source of pressurized air; the main inspiratory valve; an inhalation tube; an exhalation tube; an exhalation valve; a PEEP valve; a processor; and the continuous bleed aperture;
  the method comprising activating the source of pressurized air and configuring the processor to control the valves in the ventilator system such that:
  a) during an inspiratory cycle—the main inspiratory valve is opened to air flow, the exhalation valve is closed to air flow, and the continuous bleed aperture is opened to air flow, whereupon a stream of air flowing through the main inspiratory valve combines with a stream of air flowing through the continuous bleed aperture and the combined streams flow through the inhalation tube to the patient; and
  b) during an expiratory cycle—the main inspiratory valve is closed to air flow, the exhalation valve is opened to air flow, and the continuous bleed aperture is opened to air flow, whereupon the stream of air flowing through the continuous bleed aperture flows into the inhalation tube and combines with a stream of exhaled air flowing from the patient into the exhalation tube and the combined streams flow through the exhalation valve and, whenever the pressure is above a predetermined value of PEEP, the combined streams flow through the PEEP valve out into ambient air;
  wherein the main inspiratory valve is the diaphragm valve, which comprises a diaphragm that is activated by the inspiratory valve controller to cause the diaphragm to open and close the opening.

\* \* \* \* \*